(12) United States Patent
Karagöz et al.

(10) Patent No.: US 9,632,019 B2
(45) Date of Patent: Apr. 25, 2017

(54) APPARATUS AND METHOD FOR CLEANING DEPOSITS AND ACCRETIONS FROM AN END PLATE OF A SENSOR BODY

(75) Inventors: Hasan-Özkan Karagöz, Altensteig (DE); Michael Littmann, Bietigheim-Bissingen (DE); Thilo Krätschmer, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 1202 days.

(21) Appl. No.: 13/541,938

(22) Filed: Jul. 5, 2012

(65) Prior Publication Data

US 2013/0008466 A1 Jan. 10, 2013

(30) Foreign Application Priority Data

Jul. 4, 2011 (DE) .................. 10 2011 078 617

(51) Int. Cl.
*G01N 21/15* (2006.01)

(52) U.S. Cl.
CPC ....... *G01N 21/15* (2013.01); *G01N 2021/152* (2013.01)

(58) Field of Classification Search
CPC .. G01N 21/15; G01N 2021/152; B60S 1/528; B60S 1/0402; B60S 1/02; B60S 1/04; B60S 1/06; B60S 1/561; G02B 27/0006
See application file for complete search history.

(56) References Cited

U.S. PATENT DOCUMENTS 3,832,750 A * 9/1974 Jarvinen .................. B60S 1/60
                                                15/250.002
5,860,181 A    1/1999 Maekawa
(Continued)

FOREIGN PATENT DOCUMENTS

DE        4233218 A1    4/1994
DE        69612930 T2   3/2002
(Continued)

OTHER PUBLICATIONS

German Srch Rept, Apr. 4, 2012, Munich.
Feststoffgehaltssensor TurbiMax W CUS 41 / CUS 41-W, Jan. 1998, Germany.

*Primary Examiner* — Joseph L Perrin
*Assistant Examiner* — Irina Graf
(74) *Attorney, Agent, or Firm* — Christopher R. Powers; PatServe

(57) ABSTRACT

An apparatus and method for cleaning deposits and accretions from an end plate of a sensor body, for accommodating a measuring apparatus for determining one or more physical and/or chemical, process variables. The sensor body is sealed against penetration by liquid and a wiper is provided having a wiper blade for cleaning the end plate. The wiper is arranged as a subcomponent on a peripheral, appended module, wherein geometries of the wiper and the peripheral, appended module are so embodied that the wiper in the case of rotary movement from a rest position into a cleaning position, with the lower edge of the wiper blade being flush with the upper edge of the end plate, in the cleaning position, and in order that the wiper cleans the end plate by contact of the wiper blade with the end plate, and the wiper then returns to the rest position.

11 Claims, 4 Drawing Sheets

(56) References Cited

U.S. PATENT DOCUMENTS

| | | | |
|---|---|---|---|
| 6,905,078 B1 * | 6/2005 | Gattuso | B05B 3/0413 |
| | | | 239/11 |
| 8,069,706 B2 | 12/2011 | Battefeld | |
| 2003/0233723 A1 | 12/2003 | Lizotte | |
| 2008/0243411 A1 | 10/2008 | Pritzke | |
| 2009/0229067 A1 * | 9/2009 | Becker | A61B 1/00087 |
| | | | 15/250.361 |
| 2009/0301175 A1 * | 12/2009 | Battefeld | G01N 29/032 |
| | | | 73/53.01 |

FOREIGN PATENT DOCUMENTS

| | | | | |
|---|---|---|---|---|
| DE | 102007014844 B3 | 6/2008 | | |
| DE | 102007023480 A1 | 11/2008 | | |
| EP | 0590487 A1 | 6/1994 | | |
| EP | 1816462 B1 | 4/2011 | | |
| GB | 2098467 A * | 11/1982 | | B60S 1/185 |
| WO | 2008141874 A2 | 11/2008 | | |

* cited by examiner

APPARATUS AND METHOD FOR CLEANING DEPOSITS AND ACCRETIONS FROM AN END PLATE OF A SENSOR BODY

TECHNICAL FIELD

The invention relates to an apparatus and method for cleaning deposits and accretions from an end plate of a sensor body, wherein the sensor body is embodied for accommodating a measuring apparatus for determining one or more physical and/or chemical, process variables, wherein the sensor body is sealed against penetration by liquid and wherein a wiper is provided having a wiper blade for cleaning the end plate.

BACKGROUND DISCUSSION

Sensors in the sense of this invention serve for ascertaining process variables in liquids, especially fresh- and, industrial water, as well as in gases. Examples of typical process variables are turbidity, solids content and sludge level. Forms of embodiment can, however, concern other chemical and physical, process variables. To be mentioned here are determining nitrate content, UV absorption, pressure measurement or contactless fill level measurement, especially by ultrasound. Measuring devices suitable for determining the corresponding process variables are available from the group of firms, Endress+Hauser, in a large number of variants.

Usually, the sensors are arranged in a sensor body. Many of the mentioned process variables are optically determined. In such case, electromagnetic waves of a certain wavelength are received through an optical window in the sensor body. Known from DE 42 33 218 C2 is an apparatus for turbidity measurement, wherein, supplementally, an optical source is provided, which is connected with the sensor body via another optical window.

Known from EP 1 816 462 B1 is an arrangement, in the case of which only one window is provided for source and receiver.

If the process variables are non-optically determined, the sensor contacts the medium via a membrane or a corresponding adapting layer.

Through operation in aqueous or gaseous media, especially also wastewater, scale formations, fouling, deposits and accretions occur on the optical window or the membrane, whereby measurement results are corrupted or the measurement made impossible. Known from the brochure "Technical information TurbiMax W CUS41/CUS41-W" of the group of firms, Endress+Hauser, is that windows can be cleaned by a wiper mounted on the end plate of the sensor body.

The wiper is driven by a motor in the sensor body, wherein the movement is transmitted by means of a shaft. It must be heeded that the position where the shaft passes through the sensor body is sealed stably over the long term, in order that no medium can penetrate into the sensor body.

The movement of the wiper is controlled by a control unit and occurs alternately in, and counter to, the clockwise direction.

For preventing defective measurements, after ending the cleaning, the wiper must be brought into a defined resting position, which is positioned far enough removed from the windows. If the wiper is too near to the measuring apparatus, the measurement is disturbed and corrupted by the wiper.

SUMMARY OF THE INVENTION

An object of the present invention is to provide apparatus and method assuring reliable cleaning of the end plate of a sensor body.

The object is achieved relative to the apparatus of the invention by features including that the wiper is arranged as a subcomponent on a peripheral, appended module of the sensor body. The geometries of the wiper and the peripheral, appended module are so embodied that the wiper in the case of rotary movement in the course of a revolution moves from a rest position into a cleaning position. In the cleaning position, the lower edge of the wiper blade is flush with the upper edge of the end plate. In this way, the wiper cleans the end plate by contact of the wiper blade with the end plate, and the wiper then returns to the rest position.

The arrangement of the invention of the wiper on a peripheral, appended module has advantages as follows:
  No passing of a shaft through the end plate is necessary. Thus, the danger of unsealed locations is minimized.
  In its rest position, the wiper is far enough from the surface of the end plate, and therewith, removed from the measuring apparatus. The means that the wiper does not degrade the measurement.
  The peripheral, appended module can also be mounted subsequently on any sensor body. The means the wiper is optionally retrofittable. Depending on customer request, a peripheral, appended module can be provided. The sensor body is the same, whether a wiper is applied or not, whereby production costs can be kept small.

In a preferred embodiment, the wiper moves orthogonally to the surface of the end plate from the rest position of the wiper into the cleaning position and the wiper returns orthogonally to the surface of the end plate from the cleaning position back into the rest position.

In an advantageous embodiment, an optical measuring apparatus is provided in the sensor body and at least one optical window is located in the end plate. Exactly in the case of optical measuring devices, it is necessary that the optical window, which protects the measuring apparatus from the medium, be cleaned regularly, in order to enable correct measurement.

Positioned under the optical windows is the optical measuring apparatus, which can have one or more optical components, for example, optical sensors. In a preferred form of embodiment, each optical component has its own optical window. It is, however, also an option that one common optical window for all optical components be utilized.

Optical sensors in the sense of this invention are sensors for determining turbidity, sludge level or solids content. Besides these, however, also other optical sensors, such as e.g. sensors for determining nitrate content, UV absorption, certain pressure sensors or fill level sensors, which function according to the ultrasonic principle, can be cleaned with the apparatus of the invention.

The wavelengths of the electromagnetic waves of the optical components lie typically in the near infrared, for example, at 880 nm.

There are forms of embodiment, in the case of which the process variables are determined non-optically, for example, pressure sensors. In such case, the sensor contacts the medium via a membrane or a corresponding adapting layer.

The rotary movement of the wiper can be effected manually; preferably, however, a motor is applied as drive. In this way, it is assured that the start- and stop point in time, the velocity, the number of revolutions and the direction of movement can be set and controlled exactly. The driving force of the motor is transmitted to the wiper via a shaft. It is, moreover, an option that the force transfer occurs through non rigid connections or shaftlessly, for example, through the application of a magnetic actuation.

The motor moves the wiper, for example, unidirectionally, thus either in, or counter to, the clockwise direction. Through the geometry of the wiper and the peripheral, appended module, an option is to clean the end plate exactly also when the wiper rotates in only one direction. Of course, the motor can turn in both directions and is also able to execute a back and forth movement.

In an advantageous embodiment, there is located in the region of the bottom of the wiper a first detector element and in the region of the top of the peripheral, appended module a second, corresponding detector element. These detector elements enable determination of the position and movement of the wiper, especially the number of revolutions of the wiper.

Advantageously, a control unit is provided, with which number, duration, direction of movement and velocity of the revolutions of the wiper can be determined and controlled. Thus, the user can determine how long, how rapidly and/or how often the end plate should be cleaned.

In a preferred embodiment, the geometries of the wiper and the peripheral, appended module are so embodied that the wiper, after terminating the cleaning, returns automatically, or is forced, back into the rest position. If the wiper moves in this way back in its resting position, it is always assured that the wiper is located during measurement far enough removed from the measuring apparatus and does not disturb the measurement.

Preferably, a spring element is arranged in the interior of the peripheral, appended module. This pulls the wiper back into the rest position, or keeps it in the rest position. The presence of the spring element advantageously affects the quality of the measurement, since thereby the wiper is located in phases of measurement in a remote position away from the measuring apparatus, is kept there and does not disturb the measurement.

The end plate is arranged either orthogonally or at an angle not equal to 90° with respect to the longitudinal axis of the sensor body. The last named form of embodiment is advantageous, since the measuring apparatus can be installed shock protectedly and less dirt sensitively in the usual pipelines or at other locations.

The geometry of the peripheral, appended module and its arrangement on the sensor body, especially the height difference between the upper edge of the peripheral, appended module and the upper edge of the end plate, i.e. the height of the wiper, is preferably so embodied that deposits and accretions occurring on the wiper in the case of cleaning are scraped off as the wiper blade travels the height difference in returning to the rest position. The edge of the end plate is, in such case, embodied as a "sharp" edge, i.e. the edge of the end plate is right- or acute angled, so that fouling, which the wiper has removed from the end plate, gets scraped off from the wiper blade and the next cleaning procedure starts with a "clean" wiper blade.

The object is achieved relative to the method of the invention by features including that the sensor body is embodied for accommodating a measuring apparatus for determining one or more physical and/or chemical, process variables. In such case, the sensor body is sealed against penetration by liquid. A wiper with a wiper blade for cleaning the end plate is provided, which is arranged as a subcomponent on a peripheral, appended module. In the course of a revolution, the wiper is moved from a rest position into a cleaning position. Thus, the end plate is cleaned by contact of the wiper blade. Then, the wiper is moved back into the rest position.

In a form of embodiment, the wiper is guided from the rest position into the cleaning position by the geometry of the wiper and the peripheral, appended module, wherein the wiper travels a trajectory defined by the geometry of the wiper and the peripheral, appended module. The wiper, i.e. the wiper blade, cleans the surface of the end plate of the sensor body and sweeps then back into the rest position.

In an alternative embodiment, the wiper is moves only by an axle, shaft and the like, from the rest position into the cleaning position, the wiper, i.e. the wiper blade, cleans the surface of the end plate, and the wiper sweeps then back into the rest position.

Advantageously, the wiper returns under the action of a force automatically back into the rest position. If the wiper returns in this way in its resting position, it is always assured that the wiper is located far enough removed from the measurement and does not disturb the measurement.

The wiper is held in the rest position and the drive must overcome the force in order to move the wiper from the rest position into the cleaning position.

BRIDF DESCRIPTION OF THE DRAWINGS

The invention will now be explained in greater detail based on the appended drawing, the figures of which show as follows.

Figure 1:
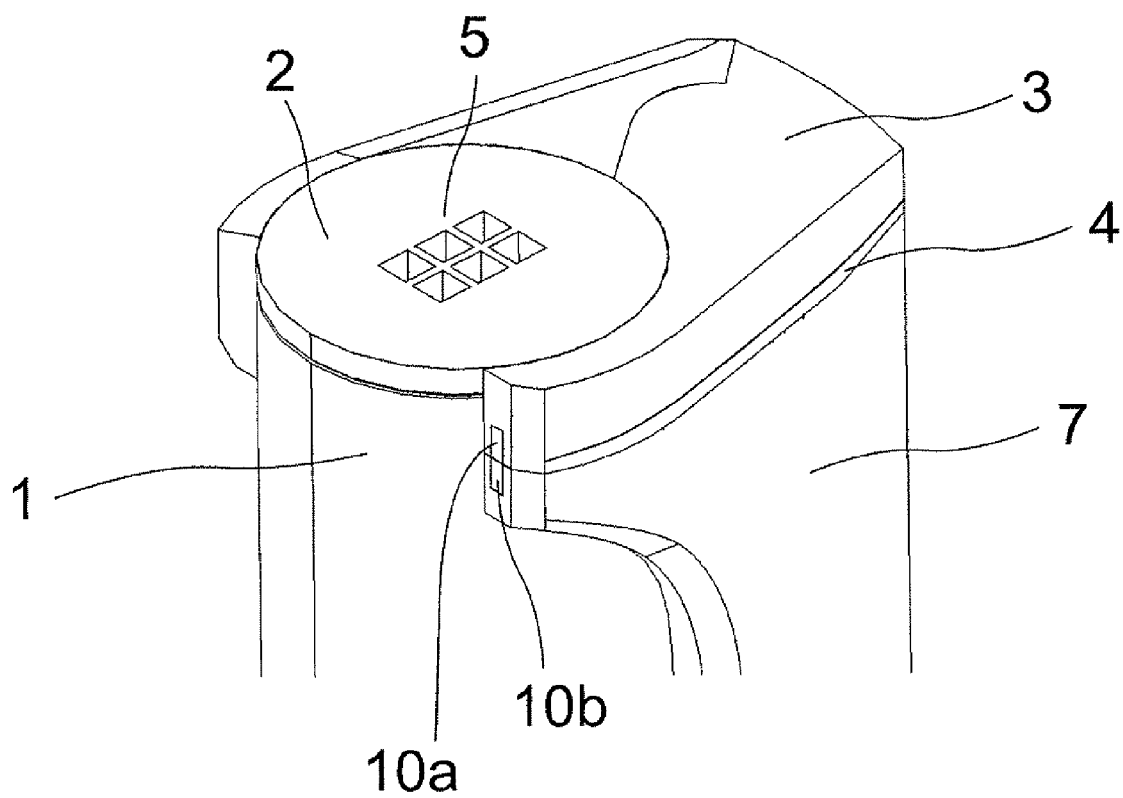
FIG. 1 is a perspective view of a sensor body with peripheral, appended module and wiper in rest position.

In the figures, equal features are provided with equal reference characters.

DETAILED DISCUSSION IN CONJUNCTION WITH THE DRAWINGS

FIG. 1 shows a sensor body 1, which is terminated sealed to liquid by an end plate 2. The end plate 2 is connected with the sensor body 1, for example, by screws, adhesive or interlocking. Sensor body 1 and end plate 2 are manufactured, for example, of stainless steel. Depending on application, embodiments comprised of hard plastic, especially PVC, POM or PPS GF 40, provide other options. Sensor body 1 and end plate 2 are preferably designed for long residence times in liquids, especially in wastewater, or in gases.

Sensor body 1 has typically the shape of a straight, circular cylinder; the end plate 2 is positioned orthogonally to the longitudinal axis LA of the sensor body. Other forms of embodiment are, however, possible. For instance, the end plate 2 can be arranged at an angle other than 90° to the longitudinal axis LA of the sensor body.

The form of embodiment in FIGS. 1 to 4 shows a measuring apparatus for determining optical, process variables. This can include, for example, turbidity, sludge level or solids content. Fundamentally, however, the apparatus of the invention can also be used for cleaning the end plate of a sensor body having a measuring arrangement for non-optical, process variables.

Located on the end plate 2 are six optical windows 5. An optical measuring apparatus 6 located therebeneath sends and receives electromagnetic waves through the windows 5, typically with wavelengths in the near infrared. The windows 5 are, for example, manufactured of sapphire glass.

In the form of embodiment illustrated in FIG. 1, the optical measuring apparatus 6 is composed of six optical components. Each optical component sends/receives through its own optical window in contact with the medium. It is, however, also an option to have the optical components transmit, respectively receive, through a window that they share in common.

In the case of the optical measuring apparatus 6, there are two independently functioning, sensor units, each having a light source and two light receivers. Preferably, the two light receivers are used for the receipt of scattered light at an angle of 90°, or 135°, to the beam direction of the light source. For example, in the case of a turbidity sensor at low turbidity values, preferably the 90°-channel is used. In the case of medium and high turbidity values as well as for solids measurements, preferably the 135°-channel is used. Other forms of embodiment have fewer, possibly more, optical components. For example, an option is a sensor unit with a light source and a light receiver with an angle of 90°, or 135°, as the case may be.

Located on the sensor body 1 is a peripheral, appended module 7. Peripheral, attached module 7 is fixedly connected with the sensor body 1 by screwed attachment, adhesive, welding and/or the like. It is to be noted that the peripheral, appended module 7 can also be subsequently mounted on the sensor body 1; the peripheral, appended module 7 is, in such case, clipped on the sensor body, e.g. clamped on by means of an adapter and secured as above described. Peripheral, attached module 7 is manufactured, for example, of a synthetic material, such as POM.

Arranged on the peripheral, appended module 7 is a wiper 3. The wiper 3 is manufactured, for instance, of hard plastic or metal. On the underside of the wiper 3 is a wiper blade 4. The wiper blade 4 serves for cleaning the end plate 2 and is produced, for example, from synthetic material, plastic, rubber or the like. The wiper blade 4 is secured by being joined to the wiper 3, especially by means of an adhesive.

In the rest position, as shown in FIG. 1, the upper edge of the wiper 3 is flush with the upper edge of the end plate 2.

Located in the region of the underside of the wiper 3, or in the region of the upper side of the peripheral, appended module 7 are corresponding detector elements 10a and 10b. Each time the wiper 3, respectively the detector element 10a, passes over the peripheral, appended module 7, respectively the detector element 10b, one revolution is detected.

Figure 4:
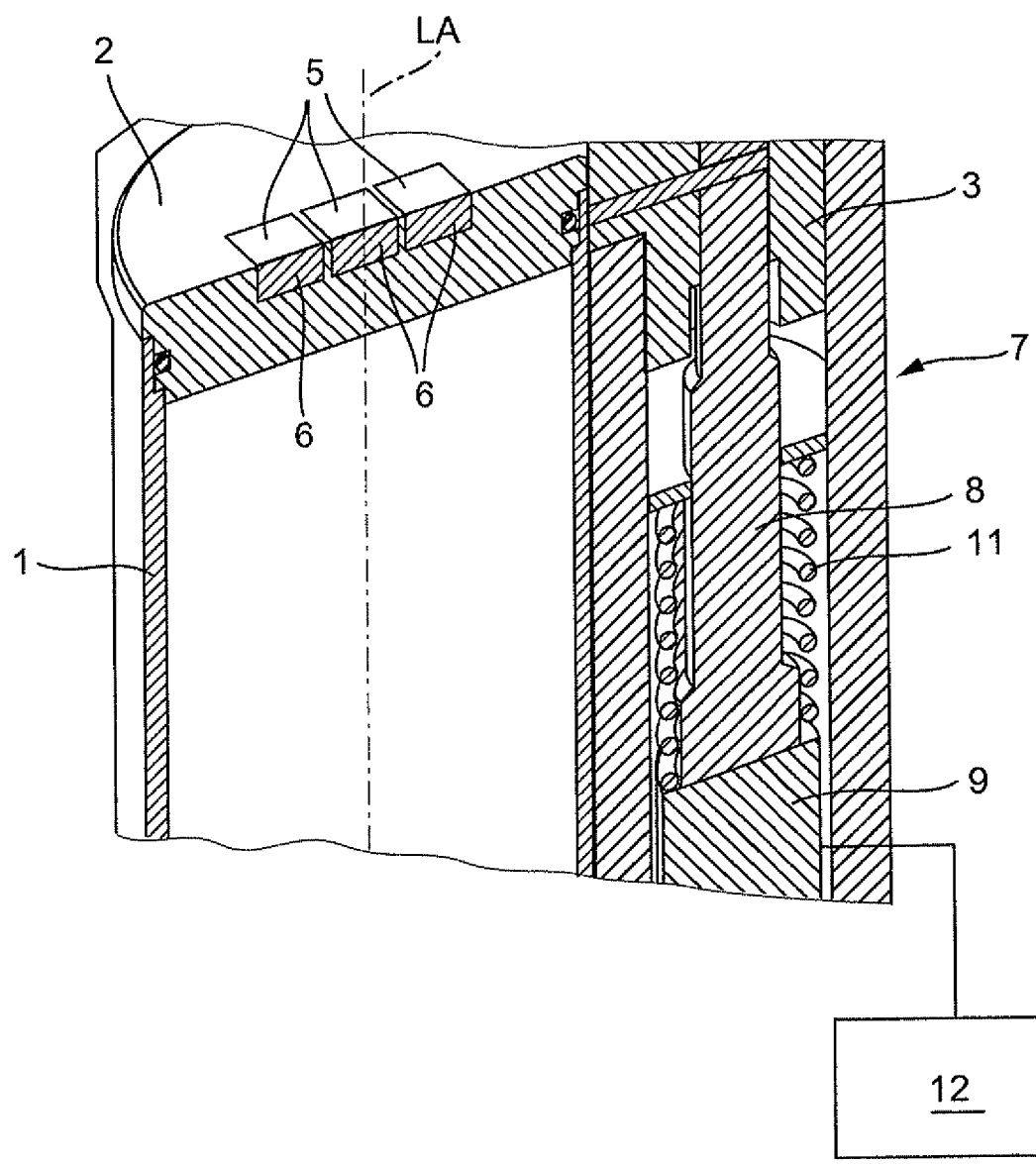
FIG. 4 is a cross section through a sensor body with peripheral, appended module and wiper in rest position.

FIG. 4 shows a cross section through the sensor body 1 in rest position. Located beneath the windows 5 are the optical measuring devices 6. A drive 9 transmits force by means of a shaft 8 to the wiper 3. The drive can be a manual drive; typically, however, a motor is used. The drive is unidirectional in the counterclockwise direction. Of course, optional forms of embodiment provide that the drive 9 rotates in the clockwise direction.

The control of the drive 9 is performed by a control unit 12. Control unit 12 controls the number of revolutions, the velocity, the direction of movement and/or the duration of the movement of wiper 3. The detector elements 10a and 10b deliver, in such connection, information concerning the position and/or movement of the wiper 3.

In the peripheral, appended module 7, above the drive 9 and around the shaft 8, is located a spring element 11. This spring element 11 effects that the wiper 3 is pulled back into, or held in, the rest position. The drive 9 must overcome this return force, in order to move the wiper 3 away from the rest position. Moreover, the spring element 11 causes the wiper 3, i.e. the wiper blade 4, to exert a defined pressure on the end plate 2 as it sweeps it.

The return force can also be applied by other components than a spring element 11, e.g. by magnetic elements mounted on the wiper 3 and the peripheral, appended module 7.

Figure 2:
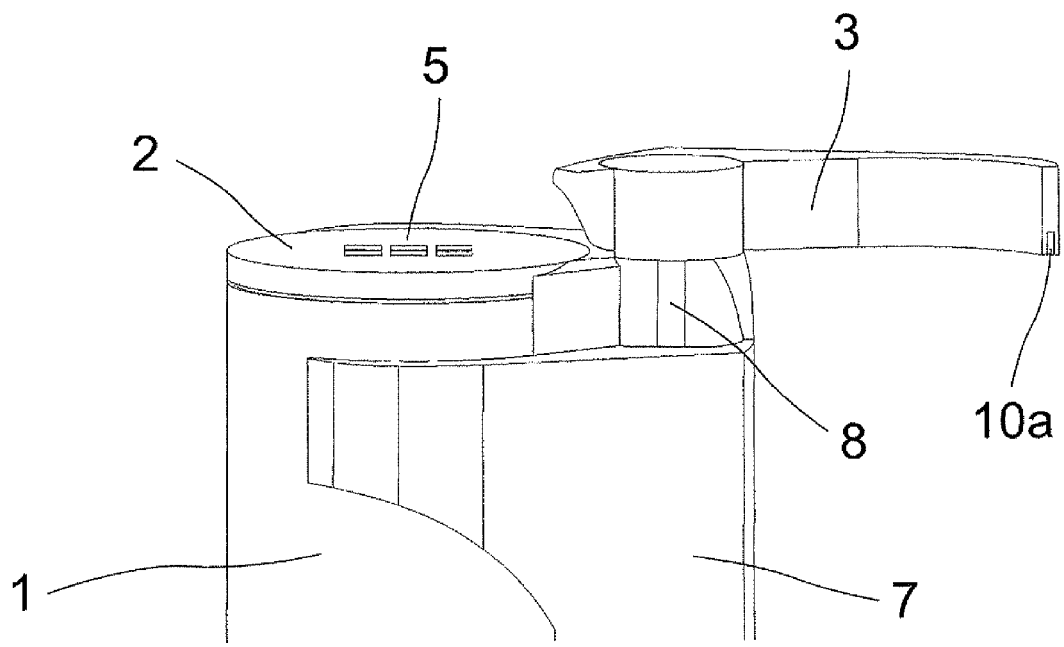
FIG. 2 is a side view of a sensor body with peripheral, appended module and wiper in an intermediate position.
Figure 3:
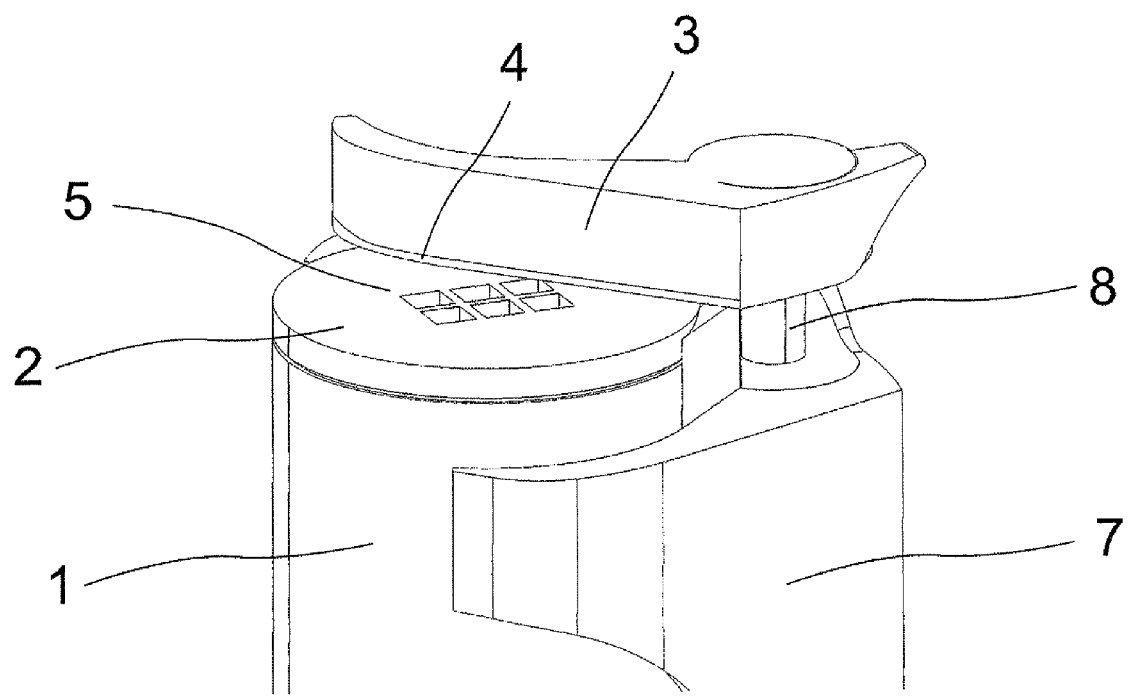
FIG. 3 is a perspective view of a sensor body with peripheral appended module and wiper in cleaning position.

FIGS. 1 to 3 show the cleaning procedure starting from rest. position (FIG. 1) through an intermediate position (FIG. 2) into a cleaning position (FIG. 3). After cleaning, the wiper 3 sweeps back into the rest position (FIG. 1).

FIG. 2 shows the sensor body 1 with the peripheral, appended module 7 in side view. If the drive 9 moves unidirectionally in the counterclockwise direction, shaft 8 causes the wiper 3 to execute a corresponding rotary movement. The geometry of the wiper 3 and of the peripheral, appended module 7 determine the trajectory, i.e. the spatial path, of the wiper 3 during the movement: The further the wiper 3 is moved by the rotary movement from the rest position, the further the wiper rises upwardly in the direction of the longitudinal axis LA of the sensor body.

In the intermediate position shown in FIG. 2, the upper edge of the wiper 3 is located above the upper edge of the end plate 2. As already mentioned, this is implemented by the particular embodiments of the wiper 3 and the peripheral, appended module 7. In rest position (FIG. 1), in contrast, the upper edge of the wiper 3 is flush with the upper edge of the end plate 2.

In the cleaning position in FIG. 3, the wiper 3 achieves its maximum height. In the cleaning position, the lower edge of the wiper blade 4 is then flush with the upper edge of the end plate 2.

Through continuous, unidirectional movement of the wiper 3, respectively the wiper blade 4, over the end plate 2, such is cleaned. Depending on the type of sensor, one or more windows 5, in given cases also membranes or adapting layers, e.g. impedance matching layers, are located on the end plate, which are likewise cleaned. An option is, moreover, to have the wiper 3 execute a back and forth movement.

After passing over the end plate 2, the wiper 3 falls back into the rest position on the peripheral, appended module 7. In addition to the drive controlled movement of the wiper 3, this happens with the assistance of the spring element 11, which, on the basis of its return force, pulls the wiper 3 back and causes the wiper 3 to snap back into its rest position.

In jumping the height difference between the upper edge of the end plate 2 and the upper edge of the peripheral, appended module 7, deposits and accretions on the wiper 3 and on the wiper blade 4 are scraped off. Supporting this is a sharp edge on the end plate 2.

Thus, one revolution of the wiper 3 is completed. The detector elements 10a and 10b detect the end of a revolution. Control unit 12 controls the number the revolutions, the duration of the cleaning, the direction of movement and/or the velocity of the wiper 3. Thus, an option is, for example, also, that, after a fixed amount of time, the wiper 3 changes its direction of movement. In the embodiment shown in FIGS. 1 to 4, this means a directional change from originally in the counterclockwise direction to now in the clockwise direction. Based on the geometry of the wiper 3 and the peripheral, appended module 7, the wiper 3 moves in the reverse direction until it returns to the rest position, where it is detected by the detector elements 10a and 10b.

A cleaning procedure is composed of at least one revolution; it can, however, be set to as many revolutions as desired or to a certain amount of time.

The invention claimed is:

1. An apparatus comprising:
   a sensor body including an end plate having an end surface with a surface edge, wherein at least one optical window is arranged in said end plate; and
   a peripheral module at least partially surrounding the sensor body and defining a module envelope in a rest position, the peripheral module including a wiper defining at least a portion of the module envelope and having a first surface and an opposing second surface, wherein said wiper further includes a wiper blade adjacent the second surface, the wiper blade including a wiper edge opposite the second surface, defining a height difference between the first surface of the wiper and the wiper edge of the wiper blade,
   wherein the wiper is configured to extend from the rest position to a cleaning position and retract to the rest position in unidirectional rotational motion along a spatial path comprising at least one complete rotation,
   wherein in the rest position the first surface of the wiper is flush with the end surface of said end plate and is disposed within the module envelope,
   wherein in the cleaning position the wiper is extended from the module envelope such that the wiper edge of the wiper blade is flush with said end surface of said end plate, such that said wiper blade cleans said end plate by contact of said wiper edge with said end surface, and
   wherein the peripheral module and the sensor body are configured such that deposits and accretions that accumulate on said wiper blade during cleaning are scraped off as the wiper blade moves across the surface edge of said end surface of said end plate as the wiper edge traverses the height difference in returning to the rest position.

2. The apparatus as claimed in claim 1, wherein:
   said wiper moves orthogonally to the end surface of said end plate from the rest position into the cleaning position and said wiper returns orthogonally to said end surface of said end plate from the cleaning position back into the rest position.

3. The apparatus as claimed in claim 1, further comprising:
   an optical measuring apparatus disposed in said sensor body, wherein said optical measuring apparatus includes at least one optical sensor.

4. The apparatus as claimed in claim 1, further comprising:
   a motor structured to drive the movement of said wiper from the rest position to the cleaning position and back to the rest position in unidirectional rotational motion along the spatial path, wherein said motor transmits a driving force to said wiper via a shaft.

5. The apparatus as claimed in claim 4, wherein:
   said motor moves said wiper unidirectionally in, or counter to, the clockwise direction.

6. The apparatus as claimed in claim 1, further comprising:
   a first detector element and a second detector element, wherein the first detector element is located near the wiper blade of said wiper and said second detector element is located in the peripheral module adjacent the first detector element, and
   wherein said first and second detector elements are structured to provide a signal that indicates a position and/or movement of said wiper.

7. The apparatus as claimed in claim 1, further comprising:
   a control unit, which determines and/or controls the number of revolutions, duration of movement, direction of movement and/or velocity of said wiper.

8. The apparatus as claimed in claim 1, wherein
   said wiper and said peripheral module are configured such that said wiper returns automatically into the rest position, or is compelled to return into the rest position, from the cleaning position.

9. The apparatus as claimed in claim 1, further comprising:
   a spring element in said peripheral module, wherein the spring element is configured to pull said wiper back into the rest position from the cleaning position, or to hold said wiper in the rest position.

10. The apparatus as claimed in claim 1, wherein:
    said end surface of said end plate is arranged either orthogonally or at an angle not equal to 90° relative to a longitudinal axis of said sensor body.

11. The apparatus as claimed in claim 1, wherein:
    the peripheral module includes a module edge configured such that deposits and accretions that accumulate on said wiper blade during cleaning are scraped off as said wiper blade moves across the module edge as wiper edge travels the height difference in returning to the rest position.

* * * * *